(12) United States Patent
Asano

(10) Patent No.: US 6,574,573 B1
(45) Date of Patent: Jun. 3, 2003

(54) SPECTRUM ANALYSIS AND DISPLAY METHOD TIME SERIES

(75) Inventor: Fumitaka Asano, Urawa (JP)

(73) Assignee: Gram Corporation (JP)

( * ) Notice: Subject to any disclaimer, the term of this patent is extended or adjusted under 35 U.S.C. 154(b) by 0 days.

(21) Appl. No.: 09/465,356

(22) Filed: Dec. 16, 1999

(30) Foreign Application Priority Data

Oct. 27, 1998 (JP) .......................................... 10-305117

(51) Int. Cl.[7] .......................... G06F 15/42; G01R 23/16
(52) U.S. Cl. .................. 702/76; 324/76.19; 324/76.28; 382/170; 600/509; 702/77
(58) Field of Search .................. 702/76, 77; 324/76.19, 324/76.28; 600/508, 509, 546; 607/40; 375/334; 367/125

(56) References Cited

U.S. PATENT DOCUMENTS

| 4,093,989 | A | * | 6/1978 | Flink et al. | 324/76.28 |
| 4,567,610 | A | * | 1/1986 | McConnell | 382/170 |
| 4,973,897 | A | * | 11/1990 | Ohsawa | 324/76.19 |
| 5,047,995 | A | * | 9/1991 | Wells | 367/125 |
| 5,273,049 | A | * | 12/1993 | Steinhaus et al. | 600/508 |
| 5,299,118 | A | * | 3/1994 | Martens et al. | 600/509 |
| 5,485,395 | A | * | 1/1996 | Smith | 702/77 |
| 5,795,304 | A | * | 8/1998 | Sun et al. | 600/546 |
| 5,894,499 | A | * | 4/1999 | Katayama et al. | 375/334 |
| 5,995,872 | A | * | 11/1999 | Bourgeois | 607/40 |
| 6,249,697 | B1 | * | 6/2001 | Asano | 600/546 |

FOREIGN PATENT DOCUMENTS

| JP | 48-37978 | 6/1973 |
| JP | 55-146133 | 11/1980 |
| JP | 58-132673 | 8/1983 |
| JP | 2-36364 | 2/1990 |
| JP | 8-65193 | 3/1996 |

* cited by examiner

Primary Examiner—Michael Nghiem
Assistant Examiner—John Le
(74) Attorney, Agent, or Firm—Schmeiser, Olsen & Watts

(57) ABSTRACT

A spectrum analysis method and apparatus for processing and displaying time series data. The time series data in digital form is decomposed into a plurality of frequency components by means of a set of band pass filters. Adjacent band pass filters have their cut-off frequencies shifted or offset from each other by their passing band widths. Amplitude information of the frequency components may be obtained. For example, the frequency components generated by the band pass filters may be sampled in amplitude at predetermined time intervals. Such sampled amplitudes are then transformed into corresponding densities of a predetermined color including a gray color according to a color (or gray) scale, and displayed on a screen on the basis of a time base of the screen.

21 Claims, 2 Drawing Sheets

SPECTRUM ANALYSIS AND DISPLAY METHOD TIME SERIES

BACKGROUND OF THE INVENTION

1. Field of the Invention

The present invention relates to a spectrum analysis and a display method of time series data derived from a series of signal issued from a living organism, wherein: in the spectrum analysis method, the series of signals issued from the living organism are sampled in amplitude at predetermined time intervals and converted into digital form through an analog-to-digital conversion processing and the like to obtain a time series data, which data thus obtained is then decomposed into a plurality of frequency components each of which is determined in amplitude; and, in the display method, variations in amplitude of the frequency components of the time series data are transformed into corresponding densities of a predetermined color including a gray color according to a predetermined color scale or a predetermined gray (i.e., white-to-black) scale and, and displayed on a display screen on the basis of a time base of the display screen.

2. Description of the Related Art

Heretofore, in most cases, a conventional spectrum analysis method has been performed through the "fast Fourier transformation (i.e., FTT)" processing. Also used is a so-called MEM (i.e., Maximum Entropy Method), which makes it possible to perform a necessary spectrum analysis of time series data even when the time series data is based on a series of signals issued for a relatively short period of time. These spectrum analyses of the time series data are performed at regular intervals of time to obtain necessary results, which are displayed in a three-dimensional data diagram on a display screen.

However, in case that information of the living organism is processed through the fast Fourier transformation processing: the larger the frequency resolution, the slower the spectrum analysis of the time series data will be performed through the fast Fourier transformation processing. Consequently, in case that the fast Fourier transformation processing is used to deal with the time series data varying in a relatively short period of time, when a period of time required to perform such spectrum analysis is reduced, variations in amplitude of the frequency components of the time series data become hard to detect. On the other hand, when the period of time required to perform the spectrum analysis of the time series data is increased to improve, in frequency resolution, the three-dimensional data diagram showing the frequency components of the time series data, variations in amplitude of the frequency components of the time series data become hard to detect.

Further, due to the dispersion in spectrum of the time series data caused by discontinuity appearing in each of the opposite ends of an analysis region characteristic of the Fourier transformation processing, it is hard for the Fourier transformation processing to detect both of: variations in amplitude of the frequency components of the time series data, which variations appear in a relatively short period of time; and, relatively small variations in frequency of the frequency components of the time series data. This is one of drawbacks of the Fourier transformation processing in dealing with the time series data.

In most cases, the signal issued form the living organism varies in a relatively short period of time. Under such circumstances, it is very important to grasp the entire variations in mode of the signal occurring in such a short period of time. However, heretofore, the Fourier transformation processing has been used to grasp variations in frequency of the signal, and, therefore suffered from its relatively long period of analysis time, which makes it impossible to detect the variations in mode of the signal appearing in such a short period of time.

For example, in the case of an electrocardiogram with a frequency resolution of 1 cpm (i.e., cycle per minute), only a result obtained in spectrum analysis of the time series data is an average value (i.e., mean information) of a series of signals issued from a patient's heart for one minute. However, in general, an abnormal irregular rhythm called "arrhythmia" of the patient's heartbeats has a few seconds' duration. Consequently, variations in amplitude of frequency resulted from the Fourier transformation processing of such "arrhythmia" are extremely small, which makes it impossible to grasp the entire activity mode of the patient's heart.

On the other hand, in the case of the above-mentioned MEM (i.e., Maximum Entropy Method), a value of amplitude in frequency of the time series data obtained through the MEM is not stable and therefore not reliable. Due to this, there is not recognized any relationship between the distribution in spectrum of the frequency components of the time series data and the time series data itself. Consequently, the MEM is not used in preparation of the electrocardiogram. In the case of the electrocardiogram and like diagrams having been already known in waveform in its meaning in detail, it is considered inadequate to employ the spectrum analysis which is not reliable in amplitude of a weak one of the frequency components of the time series data.

Further, in general, the results of the spectrum analyses periodically performed are represented by using a three-dimensional diagram. However, such a three-dimensional diagram suffers from the disadvantage that the amplitude of the weak one of the frequency components of the time series data is often hidden by a larger amplitude of another frequency component disposed in front of the weak frequency component in the diagram, which poses another disadvantage that it is hard to grasp the entire variations in mode of the frequency components of the time series data varying with elapsed time. Further, it is necessary for a desired display method to enable a doctor to grasp the entire variations in mode of the frequency components of the time series data in a relatively short time and also grasp the amplitude of the weak frequency component of the time series data even when a conventional type of spectrum analysis method is performed to display its results on the display screen by using a color map or diagram.

As described above, the fast Fourier transformation (i.e., FFT) processing and the MEM (i.e., Maximum Entropy Method) both having heretofore been used in the spectrum analysis of the time series data suffer from various problems in dealing with the signals issued from the living organism and like signals varying in a relatively short period of time.

SUMMARY OF THE INVENTION

Consequently, it is an object of the present invention to provide a spectrum analysis method and a display method of time series data derived from a series of signals issued from a living organism, which enables a doctor to precisely grasp variations in mode of frequency components of the time series data and also grasp variations in amplitude of even a weak one of the frequency component of the time series data.

In accordance with a first aspect of the present invention, the above object of the present invention is accomplished by providing:

A spectrum analysis method of time series data derived from a series of signals issued from a living organism, the signals being converted into digital form of the time series data, comprising:
a step for decomposing the time series data into a plurality of frequency components by means of a set of band pass filters, wherein the band pass filters have their cut-off frequencies shifted or offset from each other by their passing band widths, respectively, so that amplitude information of the frequency components of the time series data is obtained.

In accordance with a second aspect of the present invention, the above object of the present invention is accomplished by providing:

A display method of time series data derived from a series of signals issued from a living organism, the signals being converted into digital form of the time series data, comprising the steps of:
decomposing the time series data into a plurality of frequency components by means of a set of band pass filters, wherein the band pass filters have their cut-off frequencies shifted or offset from each other by their passing band widths, respectively;
sampling in amplitude the frequency components of the time series data at predetermined time intervals;
converting the thus sampled amplitudes of the frequency components of the time series data into corresponding densities of a predetermined color including a gray color, according to a predetermined gray scale or a predetermined color scale; and
displaying variations in the corresponding densities of the predetermined color including the gray color on a display screen on the basis of a time base of said display screen.

In other words, in order to accomplish the above object, the present invention provides a processing means for dealing with the time series data through the individual digital band pass filters.

In operation, these digital band pass filters decompose the time series data into the plurality of the frequency components.

In this processing means of the present invention: the number of the digital band pass filters is the same as that of the passing band widths; and, the digital band pass filters have their cut-off frequencies shifted or offset from each other by their passing band widths, respectively. In operation, the processing means of the present invention is capable of detecting any variations in amplitude of the frequency components in a relatively short period of time.

Further, since the set of the digital band pass filters having the above construction may continuously carry out the spectrum analysis of the time series data, there is no fear that the processing means of the present invention suffers from any dispersion in spectrum caused by discontinuity appearing in the Fourier transformation processing. Consequently, in the processing means of the present invention, it is possible for the doctor to precisely grasp even a slight variation in amplitude of the frequency components of the time series data, and also possible to precisely grasp any variations occurring in a relatively short period of time in amplitude of the frequency components of the time series data.

A response time required to perform the spectrum analysis of the time series data into the frequency components is dependent on delay times of the digital band pass filters. For example, in the case of the processing means of the present invention using the digital band pass filters each having a passing band width of 1 cpm, a necessary delay time is approximately six seconds, which is only one tenths as long as the conventional analysis using the Fourier transformation processing required. This means that the processing means of the present invention is capable of performing the spectrum analysis of the time series data in a relatively short period of time. Further, in the processing means of the present invention having the above construction: for wider values of the passing band widths of the digital band pass filters used in the processing means, the response time of the processing means becomes shorter in a substantially inverse proportion manner.

In the display method of the present invention: the set of the digital band pass filters are used to decompose the time series data into the frequency components; the thus decomposed frequency components of the time series data are then sampled in amplitude at predetermined time intervals; the thus sampled amplitudes of the frequency components are transformed into the corresponding densities of a predetermined color including a gray color; these corresponding densities of the predetermined color thus obtained are then displayed in a diagram on a display screen on the basis of a time base of the display screen. Consequently, in contrast with the prior art, the display method of the present invention having the above construction is free from a fear that the amplitude of a weak one of the frequency components of the time series data is hidden by the amplitude of another larger frequency component disposed in front of such weak frequency component. Due to the above fact, it is possible for the display method of the present invention to display the entire results of the spectrum analysis of the time series data in the diagram, and thereby enabling the doctor to clearly grasp the entire variations in amplitude of the frequency components of the time series data on the display screen.

BRIEF DESCRIPTION OF THE DRAWINGS

The above and other objects, advantages and features of the present invention will be more apparent from the following description taken in conjunction with the accompanying drawings in which.

DETAILED DESCRIPTION OF THE PREFERRED EMBODIMENTS

The best modes for carrying out the present invention will be described in detail using embodiments of the present invention with reference to the accompanying drawings.

Filters used in the present invention are digital band pass filters for dealing with time series data of digital form. Although there is no limitation on types of these band pass filters, digital Butterworth band pass filters of a so-called "IIR (i.e., Infinite Impulse Response)" type are used in the following embodiments of the present invention. In their set or bank: these digital band pass filters for dealing with the time series data are shifted or offset in their cut-off frequencies from each other by their passing band widths, respectively; and, the number of these digital band pass filters is the same as that of the frequency bands of the time in series data being subjected to the spectrum analysis.

For example, in the case of the electrocardiogram, when the frequency bands of the time series data to be analyzed range from 20 to 120 cpm, it is necessary to prepare 101 pieces of the digital band pass filters which are different from each other in their passing bandwidths. When a series of signals issued from a patient's heat are sampled at predetermined time intervals through these digital band pass filters, it is possible to obtain a plurality of frequency components each having its amplitude be proportional to its intensity as is in the Fourier transformation processing performed in the prior art.

The above data processing through these digital band pass filters is continuously performed with respect to the time series data. Due to such continuous performance of the data processing of the time series data, it is possible for the present invention to prevent any dispersion in spectrum from occurring, which dispersion in spectrum is inherent in the Fourier transformation processing in the prior art. Consequently, in the present invention, it is possible to precisely detect any amplitude of even a weak one of the frequency components of the time series data.

Figure 1:
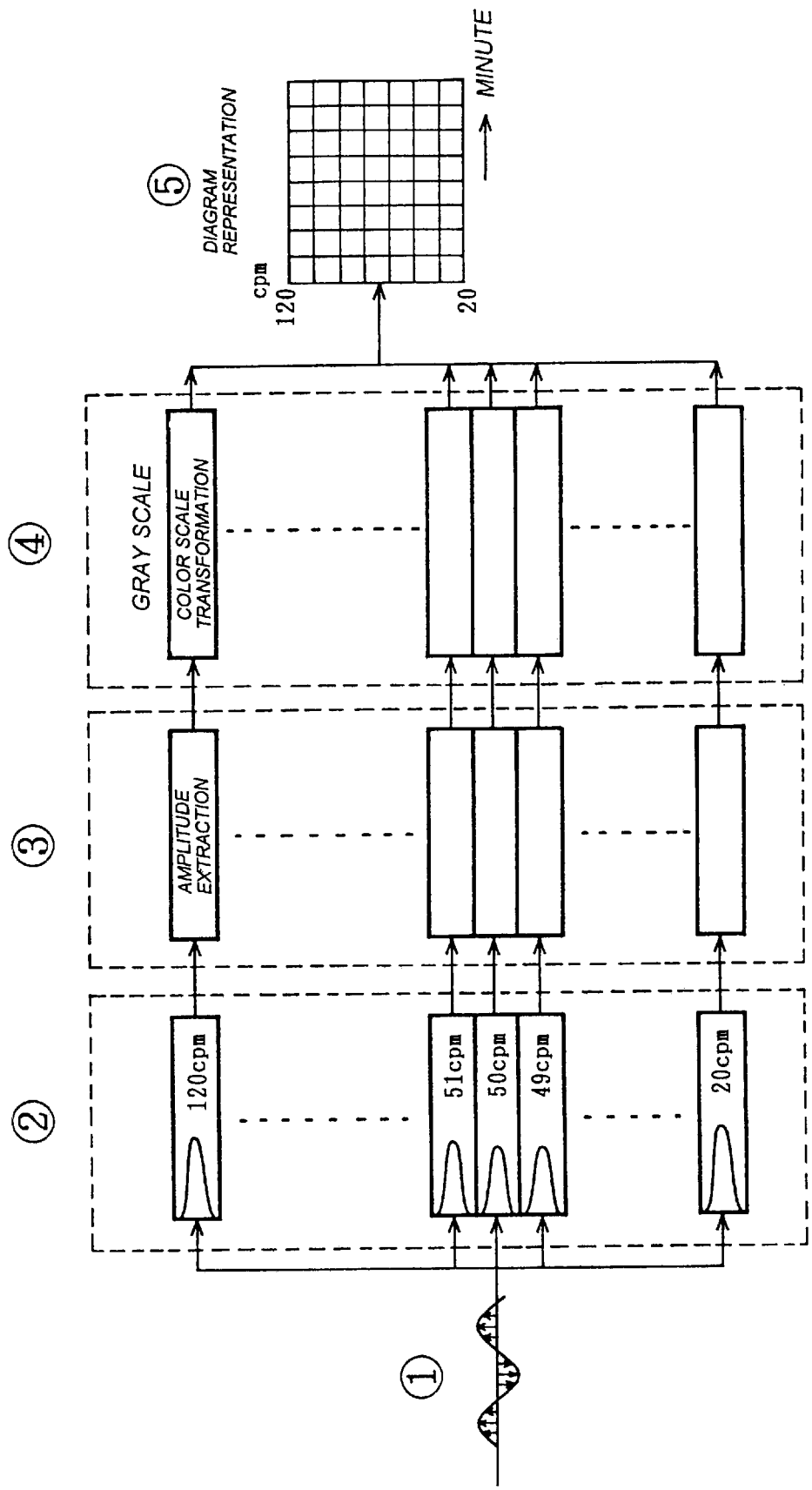
FIG. 1 is a schematic block diagram of the processing means of the present invention, illustrating flows of information or data.

Now, a spectrum analysis method and a display method of spectrum analysis of the time series data according to the present invention will be described with reference to the accompanying drawings, in which: the reference numeral 1 encircled with a circular mark denotes the time series data; and, the reference numeral 2 encircled with a circular mark denotes a set or band of the digital band pass filters. By using the bank 2 of these digital band pass filters, the time series data is decomposed into a plurality of frequency components which are then sampled in amplitude at predetermined time intervals through an amplitude extraction bank denoted by the reference numeral 3 encircled with a circular mark, as shown in FIG. 1 in which the amplitude extraction bank 3 is disposed in the downstream side of the band 2.

Incidentally, the frequency components of the time series data vary in amplitude when they are extracted in the amplitude extraction bank 3. Consequently, it is also possible to extract in amplitude the frequency components of the time series data at the midpoint of a period of time during which the amplitude extraction processing of the frequency components is performed (hereinafter referred to as the amplitude extraction period of time). Preferably, the entire waveform of the frequency components of the time series data existing in the amplitude extraction period of time is divided into a plurality of waveform segments each corresponding to each of the frequency components, so that the amplitudes of these frequency components are sampled. After that, an average value (i.e., mean value) of the thus sampled amplitudes of the frequency components is calculated and used in the methods of the present invention.

The thus sampled amplitudes of the frequency components of the time series data are then transformed into corresponding densities of a predetermined color including a gray color according to a predetermined color scale or a predetermined gray scale. This amplitude-to-color density transformation is performed after setting a gain of the scale and the amount of offset values for the purpose of facilitating the production of necessary information. The results of the spectrum analysis of the time series data after transformed into the densities of the predetermined color according to the color scale or the gray scale are displayed in a diagram (denoted by the reference numeral 5 encircled by a circular mark in FIG. 1 and displayed on a display screen) on the basis of each of the frequency components and the time base of the display screen.

Figure 2:
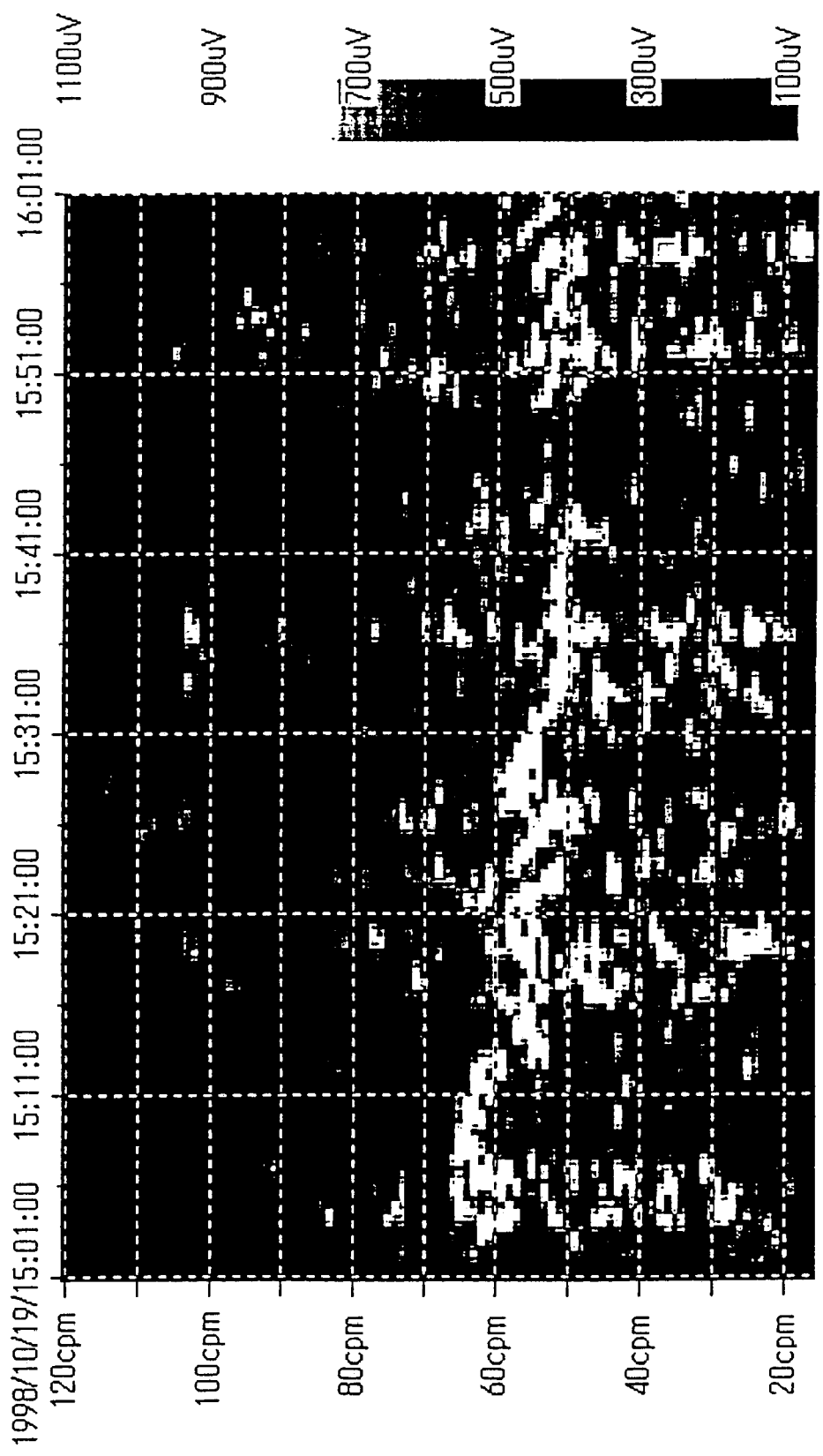
FIG. 2 is a schematic diagram of the time series data processed and displayed according to both the spectrum analysis method and the display method of the present invention, illustrating the results of the spectrum analysis of the time series data, which results are transformed into the corresponding densities of the gray color according to the predetermined gray scale, and displayed on the display screen on the basis of the time base of the display screen.

Although there are various ways for displaying the diagram, one example is shown in FIG. 2, in which: the horizontal axis represents the time base of the time series data in the diagram; the vertical axis represents in frequency the frequency components of the time series data; and, the densities of the predetermined color or gray color in the diagram of FIG. 2 show the results of the spectrum analysis of the time series data according to the spectrum analysis method and the display method of the present invention. As is clear from the diagram of FIG. 2, it is possible to immediately grasp the variations in amplitude of the frequency components of the time series data varying with time. As for the variations in amplitude of a weak one of the frequency components of the time series data (which variations are hard to detect in the prior art), it is also possible for the methods of the present invention to immediately grasp them. In other words, by using the methods of the present invention, the doctor is capable of immediately grasp the entire variations of the frequency components of the time series data.

Next, concrete examples of arithmetic operations performed in the digital band pass filters will be described in detail.

The digital band pass filters used here are constructed of a plurality of vertically connected inter-digital (i.e., ID) type band pass filters such as digital Butterworth band pass filters of 4th order each having: an analog-to-digital (i.e., A/D) conversion speed of 10 samples/sec; a center frequency of 50 cpm; and, a passing band width of 1 cpm.

Re: Filter Constants:

num [0]=1.0, num [1]=0.0, num [2]=−1.0,
num [3]=1.0, num [4]=0.0, num [5]=−1.0;
den [0]=1.0, den [1]=−1.7178023, den [2]=0.98955997
den [3]=1.0, den [4]=−1.7283111, den [5]=0.98974543;
scale=0.000053534792;

Re: Arithmatic Operations:

sum=data×scale;
for (i=0; i<2; i++) {
aw=num [i×3+1]×delay [2×i]+num [i×3+2]
×delay [2×i+1];
bw=den [i×3+1]×delay [2×i]+den [i×3+2]
×delay [2×i+1];
wo=sum−bw;
sum=wo×num [i×3]+aw;
delay [2×i+1]=delay [2×i];
delay [2×i]=wo;
}
input the time series data to "delay", and output the resultant to "sum".

Since the present invention has the above construction, by using the present invention it is possible to perform the spectrum analysis of the time series data which varies in a relatively short period of time. According to the present invention, also the variations in amplitude of a weak one of the frequency components of the time series data may be grasped or detected in an easy manner, which variations is hard to detect in the prior art. The present invention may be effectively applied to preparation of the electrocardiogram and also to analysis of an electroencephalogram (i.e., EEG).

For example, as for the electrocardiogram, since the electrocardiogram shows a periodic data, abnormal signals (i.e., abnormalities) appear in an extremely small area of such periodic data in most cases. On the other hand, when a Holter electrocardiograph is used for a long period of time, a large amount of data is produced thereby. Consequently, in order to find out the abnormalities among such large amount of data, in a conventional method for finding out such abnormalities, variations in "R—R" interval serving as a standard measure of the length of the patient's heartbeats have heretofore been referred to. However, the variations in "R—R" interval have made substantially no indication of such abnormalities in most cases. Consequently, in the conventional method, there is a high possibility of overlooking various types of important information included in the electrocardiogram.

Since it is known to be able to obtain various types of clinical findings by using the electrocardiogram on the basis of fine variations in waveforms of data shown in the electrocardiogram, it is possible for the display method of the present invention to have the doctor immediately grasp the entire variations in amplitude of even a weak one of the frequency components of the time series data when the results of the spectrum analysis of the time series data are displayed in the diagram on the display screen on the basis of the time base of the display screen according to the display method of the present invention, which further enables the doctor to immediately find out the abnormalities of the time series data in an easy manner even when the time series data is obtained for a long period of time, and therefore enormous in volume.

What is claimed is:

1. A spectrum analysis method, comprising:
   decomposing time series data in digital form into a plurality of frequency components by means of a set of band pass filters, wherein adjacent band pass filters of said band pass filters have their cut-off frequencies shifted or offset from each other by their passing band widths, and wherein said cut off frequencies of said adjacent band pass filters cannot be shifted or offset from each other by their passing band widths if said cut-off frequencies of said adjacent band pass filters are equal to each other.

2. The method of claim 1, further comprising converting signals issued from a living organism into said time series data in digital form.

3. The method of claim 2, wherein if said signals include an abnormal signal then an amplitude of a frequency component relating to said abnormal signal cannot be hidden by a larger amplitude of any other of said frequency components.

4. The method of claim 2, wherein said signals comprise electrocardiogram signals.

5. The method of claim 1, further comprising obtaining amplitude information of said frequency components, after said decomposing.

6. The method of claim 5, wherein a response time for said obtaining said amplitude information varies in a substantially inverse manner with band widths of said band pass filters.

7. The method of claim 1, wherein an amplitude of each of said frequency components cannot be hidden by a larger amplitude of any other of said frequency components.

8. The method of claim 1, wherein said band pass filters comprise Butterworth band pass filters.

9. The method of claim 1, wherein each band pass filter has a same band width.

10. A display method of time series data derived from a series of signals issued from a living organism, said signals being converted into digital form of said time series data, comprising the steps of:
    decomposing said time series data into a plurality of frequency components by means of a set of band pass filters, wherein said band pass filters have their cut-off frequencies shifted or offset from each other by their passing band widths, respectively;
    sampling in amplitude said frequency components of said time series data at predetermined time intervals;
    converting the thus sampled amplitudes of said frequency components of said time series data into corresponding densities of a predetermined color including a gray color, according to a predetermined gray scale or a predetermined color scale; and
    displaying variations in said corresponding densities of said predetermined color including said gray color on a display screen on the basis of a time base of said display screen.

11. An apparatus, comprising:
    a set of band pass filters for decomposing time series data in digital form into a plurality of frequency components, wherein adjacent band pass filters of said band pass filters have their cut-off frequencies shifted or offset from each other by their passing band widths;
    sampling means for sampling in amplitude said frequency components at predetermined time intervals;
    converting means for converting said sampled amplitudes of said frequency components into corresponding densities of a predetermined color including a gray color, according to a predetermined gray scale or a predetermined color scale; and
    displaying means for displaying variations in said corresponding densities of said predetermined color including said gray color on a display screen on the basis of a time base of said display screen.

12. The apparatus of claim 11, wherein said time series data relates to signals issued from a living organism.

13. A spectrum analysis apparatus, comprising:
    a set of band pass filters for decomposing time series data in digital form into a plurality of frequency components, wherein adjacent band pass filters of said band pass filters have their cut-off frequencies shifted or offset from each other by their passing band widths, and wherein said cut-off frequencies of said adjacent band pass filters cannot be shifted or offset from each other by their passing band widths if said cut-off frequencies of said adjacent band pass filters are equal to each other.

14. The apparatus of claim 13, wherein said time series data relates to signals issued from a living organism.

15. The apparatus of claim 14, wherein if said signals include an abnormal signal then an amplitude of a frequency component relating to said abnormal signal cannot be hidden by a larger amplitude of any other of said frequency components.

16. The apparatus of claim 14, wherein said signals comprise electrocardiogram signals.

17. The method of claim 13, further comprising means for obtaining amplitude information of said frequency components.

18. The apparatus of claim 17, wherein a response time for obtaining said amplitude information varies in a substantially inverse manner with band widths of said band pass filters.

19. The apparatus of claim 13, wherein an amplitude of each of said frequency components cannot be hidden by a larger amplitude of any other of said frequency components.

20. The apparatus of claim 13, wherein said band pass filters comprise Butterworth band pass filters.

21. The apparatus of claim 20, wherein each band pass filter has a same band width.

* * * * *

UNITED STATES PATENT AND TRADEMARK OFFICE
CERTIFICATE OF CORRECTION

PATENT NO. : 6,574,573 B1
DATED : June 3, 2003
INVENTOR(S) : Asano

It is certified that error appears in the above-identified patent and that said Letters Patent is hereby corrected as shown below:

<u>Title page,</u>
Item [75], Inventor's address, delete "Urawa" and insert -- Urawa-Shi --.

<u>Column 7,</u>
Delete lines 30-39: "decomposing time data in digital form into a plurality of frequency components by means of a set of band pass filters, wherein adjacent band pass filters of said band pass filters have their cut-off frequencies shifted or offset from each other by their passing band widths, and wherein said cut off frequencies of said adjacent band pass filters cannot be shifted or offset from each other by their passing band widths if said cut-off frequencies of said adjacent band pass filters are equal to each other," and insert -- decomposing time series data into a plurality of frequency components by means of a set of band pass filters, wherein adjacent band pass filters of said band pass filters have their cut-off frequencies shifted or offset from each other in a non-overlapping fashion by their passing band widths. --

<u>Column 8,</u>
Lines 38-43, delete "by their passing band widths, and wherein said cut-off frequencies of said adjacent band pass filters cannot be shifted or offset from each other by their passing band widths if said cut-off frequencies of said adjacent band pass filters are equal o each other." and insert -- in a non-overlapping fashion by their passing band widths. --

Signed and Sealed this

Thirtieth Day of September, 2003

JAMES E. ROGAN
*Director of the United States Patent and Trademark Office*